United States Patent
Javitch et al.

(10) Patent No.: US 10,962,538 B2
(45) Date of Patent: Mar. 30, 2021

(54) ASSAYS USING ARRESTIN RECRUITMENT AND UNMODIFIED RECEPTORS

(71) Applicant: THE TRUSTEES OF COLUMBIA UNIVERSITY IN THE CITY OF NEW YORK, New York, NY (US)

(72) Inventors: Jonathan A Javitch, Dobbs Ferry, NY (US); Maria Hauge Pedersen, Brooklyn, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 132 days.

(21) Appl. No.: 16/008,834

(22) Filed: Jun. 14, 2018

(65) Prior Publication Data
US 2019/0383808 A1 Dec. 19, 2019

(51) Int. Cl.
*G01N 33/566* (2006.01)
*C12N 9/12* (2006.01)

(52) U.S. Cl.
CPC ............ *G01N 33/566* (2013.01); *C12N 9/12* (2013.01); *C12Y 207/11016* (2013.01); *G01N 2333/4703* (2013.01); *G01N 2333/705* (2013.01); *G01N 2500/02* (2013.01)

(58) Field of Classification Search
CPC ............ G01N 33/566; G01N 2500/02; G01N 2333/705; G01N 2333/4703; G01N 2333/4719; C12N 9/12; C12Y 207/11016
See application file for complete search history.

(56) References Cited

U.S. PATENT DOCUMENTS

| 8,557,970 B2 | 10/2013 | Encell et al. |
| 8,669,103 B2 | 3/2014 | Binkowski et al. |
| 9,797,889 B2 | 10/2017 | Dixon et al. |
| 9,797,890 B2 | 10/2017 | Dixon et al. |

OTHER PUBLICATIONS

Donthamsetti et al. (2015), "Using bioluminescent resonance energy transfer (BRET) to characterize agonist-induced arrestin recruitment to modified and unmodified G protein-coupled receptors (GPCRs)", Curr. Prot. Pharmacol. 70:2.14.1-2.14.14. Available Sep. 1, 2016.
Malhotra and Erlmann (Jul. 8, 2011), "Protein export at the ER: loading big collagens into COPII carriers", EMBO 30:3475-80.
Clayton et al., "Mutation of Three Residues in the Third Intracellular Loop of the Dopamine D2 Receptor Creates an Internalizationdefective Receptor*", The Journal of Biological Chemistry vol. 289, No. 48, pp. 33663-33675, Nov. 28, 2014.
Dixon et al., "NanoLuc Complementation Reporter Optimized for Accurate Measurement of Protein Interactions in Cells", ACS Chem. Biol., 11, 400-408, Published Nov. 16, 2015.

*Primary Examiner* — Ruixiang Li
(74) *Attorney, Agent, or Firm* — Leason Ellis LLP

(57) ABSTRACT

The current invention is methods and assays for detecting and/or measuring the modification, i.e., activation or inhibition, of a receptor of interest, without the need to modify the receptor with a label or a tag. The invention uses proteins that move, translocate, are recruited and/or bind to the receptor of interest when the receptor is modified, and proteins in proximity to and/or in the same compartment as the receptor of interest. The proteins are attached or linked to polypeptides that result from the unique cleavage of a modified *Oplophorus* luciferase. When the proteins are in proximity allowing the unique polypeptides to recombine, a luminescent signal is generated. The invention also includes vector encoding these proteins, cells expressing these proteins, compositions, system and kits.

7 Claims, 8 Drawing Sheets
(7 of 8 Drawing Sheet(s) Filed in Color)
Specification includes a Sequence Listing.

Figure 1
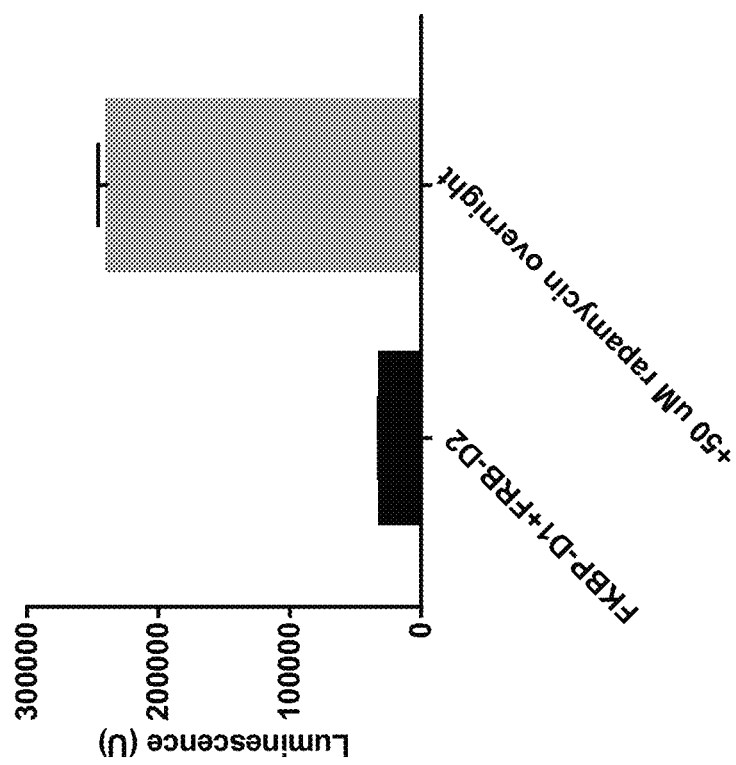
Figure 1A
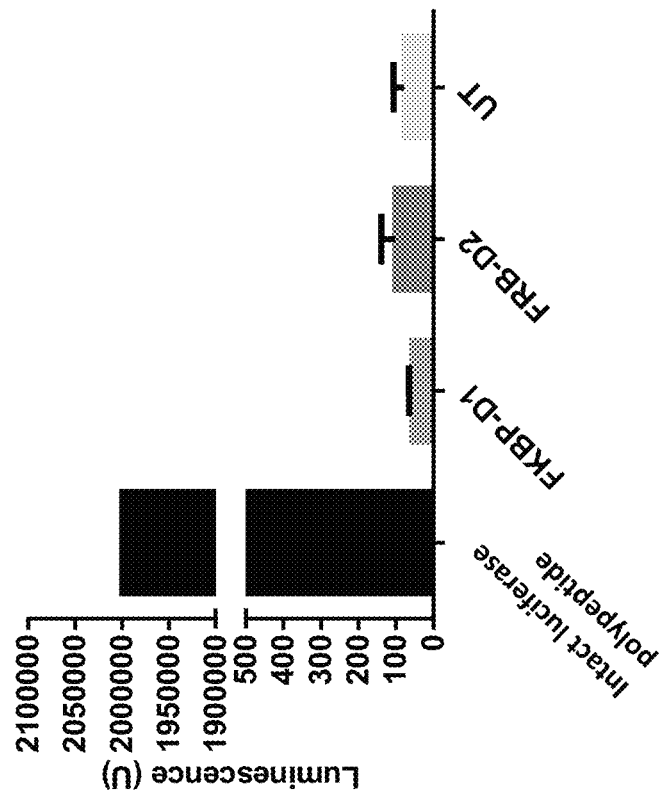
Figure 1B

Figure 2

D2-linker-Arrestin3

Nucleotide sequence:
ATGGGAGTGCTGACCCCTAACATGATGACTACTTCGGCAGAACCCTACGAGGGAATCGCCGTGTTCGACGGCAAGAATCACCCTGTGAACGGCAACCTGTGAAACGGCAACAAGATCA TCGACGAGCGGCTGAATCAACCCGACGGGCAGCCTGCTGTTCAGAGTGACGATCAATGGCGTGAAGGATGAGCTGTGCGAGAGAATTCTGGCCGGACTCAGATCTCGGCGAGC TCTCGACTCCATGGGCGGAGAAACCCGGGACAGCCTTGTGCTGTAGATGGTTCTCAAGAAATCGAGTCTCTAAGAAATCAAGCTGAGATCAGGTATCACCTGGAACAAAGTG GACCCTGTAGATGCGTGGTGCTCGTCGAACTGACTGAAGACTGTCGTATCCGCGCACTCAGAGATCTGAAGACTTGAAGAAACTGGAGCAGATG GTCCTTCCGCAAAGACCTGTTACATACCCTGCCACTAAGGTTCCAAGTGCCGTCCCTACAGAGATCTCCATGCTGAATCTGGATGATCACAGAGACCTATAAGGTCCACCTCGGGTCTGAAGACTTCGAGATTGGAGATGTG CTAAATCACTAGAGAGGAAAAGTCACAAAGGAAAGTCCCTGAACCTGGTCCTGAATCGGAAGGTGAGCCTGGAGAAGCTGCTCAAGGAGAAACCCAGTCGAATCAAGCAGG ACTTCCTCATGTCTGACTGGTTCGTGAAGCTACGTAGAGACCTACTCTTACATAGAAGGTGAAGACAGCCTAACCCTCAAGAAATCAGACCAAGCAGCTGAGAATCTCAAGAAGACCAG TCAGAAGATCAAGTCTCTGTGAGAACGAGTACCCCTGTTCAGATGCTGCACCAACCCAGTGCTCCATCTGAACGAAAGGAAAAACTCAAGAGCTCAAGAATGCATGCATGCCACGAT CATTCGTAAGGTGTACATCAATATAACCCACTTGGTGTCTCAGACCCCAGTCGAAGGGAGATCGTCTCGTGTTCATTGAAATTGATACCAACTCAACTATGCCACAAGAT CGTGAAGGAGCGGTGCAACAGCCACTGACCCATTTGCCCGGTTCACAGAAGAAGACTATGATGATCAACTCTGCTAA SEQ ID NO: 6

Amino acid sequence:
MGVTPNMMDYFGRPVEGIAVFDGKMITVTGIMGNHIDERLINPDGSLLFRVTIMGVTGWRLCERILAGLRSRRALDSMGSRPGTRVFKRSSPMCKLTVYLGKRDFVDHLDKVDPVD GVVLVDPDYLKDRKVFVTLTCAFNYGREDLVLGLSFRKDLFLATYQAFPPPRPPTRLQDRLLRKLGQHAHPFFTFPQML PCSVTLQPPRPDTGRACGVDFEIRAFCAKSLEEKSMK RNSVRILVRMVQSAPPSKPGSPQPSAFTTRHFLMSDRSIHEASLDKELYHGSPLNVNVHSVTNNSTKTVKMRVSVRCQYAPDHLFSTAQYKCPVAQLEQDGQVSPSSTFCKVTFTPLLSDN REMRGLADGKLMHEDTNLASSTIVMEGANKEVLGQVSYRVRVKLVVSRGGDVSSVELPFVLMHPKPHDHPLPRPQSAAPETDVPVDTNLREFDTRVATDDDNVFEDFARLRLKGMKDD DYDDQLC SEQ ID NO: 5

Membrane marker-linker-D1

Nucleotide sequence:
ATGTGCTGTCTGAGAAGAACAAGAACCAAGAACAGGTTCGAAAAGAATGAATGATGAGGAACCAAAAGAATGATGAGGACCTCATCATGTGAGCAAGGGCGGCGGAGGTTCCGGTGGGGGTGGCTCTGGCGGAGGTTCC GGTGGAGAGCTCCGCGGTGGAGAGCTCCGAGATGGTGTTCACCCTGGAAGATTCGTGGGGCGACTGGCGGCAGACCGCCGGCTACAATCTGGACCAGGTGCTGGAACAGGGC GGCGTGTCCAGCCTGTTTCAGAACCTGGGCGTGTCCGATGACCCCATCCAGAGAATCGTGCTGAGCGGCGAAGAACCGGCCTGAAGAGCGACATCCAGTGATCATCCCTTACGAG GGCCTGTCCGGCGACCAGATGGGCCAGATGGGCCAGATGGCCAGAGAGCCCCTTAAGGTGGTGTACCCCGGTGGACGACCACCTTCAAAGTGATCCTGCTACGGCACCCTCGTGATCGACTAA SEQ ID NO: 8

Amino acid sequence:
MLCCLRNTKQYKKLEEEDWNFVSKGGGGSGGGGSGGGGSGELRGGELEMVFTLEDFVGDWRQTAGYNLDQVLEQGGVSSLFQNLGVSVFPQRIVLSGENGLKIDIHVIPYEGLS GDQMGQMGQERIFRVVYPVDDHHFVILHVHYGTLVID SEQ ID NO: 7

B2R – Beta2 adrenergic receptor; MOR – Mu opioid receptor; D2R – Dopamine 2 Receptor; GRK2 – G protein-coupled receptor kinase 2

SEQUENCE LISTING

```
<160> NUMBER OF SEQ ID NOS: 8

<210> SEQ ID NO 1
<211> LENGTH: 102
<212> TYPE: PRT
<213> ORGANISM: Artificial Sequence
<220> FEATURE:
<223> OTHER INFORMATION: Synthetic construct

<400> SEQUENCE: 1

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His Phe Lys Val Ile Leu His Tyr
                85                  90                  95

Gly Thr Leu Val Ile Asp
            100

<210> SEQ ID NO 2
<211> LENGTH: 69
<212> TYPE: PRT
<213> ORGANISM: Artificial Sequence
<220> FEATURE:
<223> OTHER INFORMATION: Synthetic Construct

<400> SEQUENCE: 2

Gly Val Thr Pro Asn Met Ile Asp Tyr Phe Gly Arg Pro Tyr Glu Gly
1               5                   10                  15

Ile Ala Val Phe Asp Gly Lys Lys Ile Thr Val Thr Gly Thr Leu Trp
```

```
            20                  25                  30
Asn Gly Asn Lys Ile Ile Asp Glu Arg Leu Ile Asn Pro Asp Gly Ser
        35                  40                  45

Leu Leu Phe Arg Val Thr Ile Asn Gly Val Thr Gly Trp Arg Leu Cys
    50                  55                  60

Glu Arg Ile Leu Ala
65

<210> SEQ ID NO 3
<211> LENGTH: 303
<212> TYPE: DNA
<213> ORGANISM: Artificial Sequence
<220> FEATURE:
<223> OTHER INFORMATION: Synthetic nucleotide

<400> SEQUENCE: 3
atggtgttca ccctggaaga tttcgtgggc gactggcggc agaccgccgg ctacaatctg      60
gaccaggtgc tggaacaggg cggcgtgtcc agcctgtttc agaacctggg cgtgtccgtg     120 accccccatcc agagaatcgt gctgagcggc gagaacggcc tgaagatcga catccacgtg    180
atcatccctt acgagggcct gtccggcgac cagatgggcc agatcgagaa gatctttaag    240
gtggtgtacc ccgtggacga ccaccacttc aaagtgatcc tgcactacgg caccctcgtg    300
atc                                                                  303

<210> SEQ ID NO 4
<211> LENGTH: 213
<212> TYPE: DNA
<213> ORGANISM: Artificial Sequence
<220> FEATURE:
<223> OTHER INFORMATION: Synthetic nucleotide

<400> SEQUENCE: 4
gacggcgtga cccctaacat gatcgactac ttcggcagac cctacgaggg aatcgccgtg      60
ttcgacggca agaaaatcac cgtgaccggc accctgtgga acggcaacaa gatcatcgac    120
gagcggctga tcaaccccga cggcagcctg ctgttcagag tgaccatcaa tggcgtgaca    180
ggctggcggc tgtgcgagag aattctggcc tga                                 213

<210> SEQ ID NO 5
<211> LENGTH: 489
<212> TYPE: PRT
<213> ORGANISM: Artificial Sequence
<220> FEATURE:
<223> OTHER INFORMATION: Synthetic construct

<400> SEQUENCE: 5

Met Gly Val Thr Pro Asn Met Ile Asp Tyr Phe Gly Arg Pro Tyr Glu
1               5                  10                  15

Gly Ile Ala Val Phe Asp Gly Lys Lys Ile Thr Val Thr Gly Thr Leu
            20                  25                  30

Trp Asn Gly Asn Lys Ile Ile Asp Glu Arg Leu Ile Asn Pro Asp Gly
        35                  40                  45

Ser Leu Leu Phe Arg Val Thr Ile Asn Gly Val Thr Gly Trp Arg Leu
    50                  55                  60

Cys Glu Arg Ile Leu Ala Gly Leu Arg Ser Arg Ala Leu Asp Ser
65                  70                  75                  80

Met Gly Glu Lys Pro Gly Thr Arg Val Phe Lys Lys Ser Ser Pro Asn
                85                  90                  95
```

```
Cys Lys Leu Thr Val Tyr Leu Gly Lys Arg Asp Phe Val Asp His Leu
                100                 105                 110

Asp Lys Val Asp Pro Val Asp Gly Val Leu Val Asp Pro Asp Tyr
            115                 120                 125

Leu Lys Asp Arg Lys Val Phe Val Thr Leu Thr Cys Ala Phe Arg Tyr
130                 135                 140

Gly Arg Glu Asp Leu Asp Val Leu Gly Leu Ser Phe Arg Lys Asp Leu
145                 150                 155                 160

Phe Ile Ala Thr Tyr Gln Ala Phe Pro Val Pro Asn Pro Pro Arg
                165                 170                 175

Pro Pro Thr Arg Leu Gln Asp Arg Leu Leu Arg Lys Leu Gly Gln His
            180                 185                 190

Ala His Pro Phe Phe Phe Thr Ile Pro Gln Asn Leu Pro Cys Ser Val
                195                 200                 205

Thr Leu Gln Pro Gly Pro Glu Asp Thr Gly Lys Ala Cys Gly Val Asp
                210                 215                 220

Phe Glu Ile Arg Ala Phe Cys Ala Lys Ser Leu Glu Glu Lys Ser His
225                 230                 235                 240

Lys Arg Asn Ser Val Arg Leu Val Ile Arg Lys Val Gln Phe Ala Pro
                245                 250                 255

Glu Lys Pro Gly Pro Gln Pro Ser Ala Glu Thr Thr Arg His Phe Leu
                260                 265                 270

Met Ser Asp Arg Ser Leu His Leu Glu Ala Ser Leu Asp Lys Glu Leu
                275                 280                 285

Tyr Tyr His Gly Glu Pro Leu Asn Val Asn Val His Val Thr Asn Asn
                290                 295                 300

Ser Thr Lys Thr Val Lys Lys Ile Lys Val Ser Val Arg Gln Tyr Ala
305                 310                 315                 320

Asp Ile Cys Leu Phe Ser Thr Ala Gln Tyr Lys Cys Pro Val Ala Gln
                325                 330                 335

Leu Glu Gln Asp Asp Gln Val Ser Pro Ser Ser Thr Phe Cys Lys Val
                340                 345                 350

Tyr Thr Ile Thr Pro Leu Leu Ser Asp Asn Arg Glu Lys Arg Gly Leu
                355                 360                 365

Ala Leu Asp Gly Lys Leu Lys His Glu Asp Thr Asn Leu Ala Ser Ser
370                 375                 380

Thr Ile Val Lys Glu Gly Ala Asn Lys Glu Val Leu Gly Ile Gln Val
385                 390                 395                 400

Ser Tyr Arg Val Lys Val Lys Leu Val Val Ser Arg Gly Gly Asp Val
                405                 410                 415

Ser Val Glu Leu Pro Phe Val Leu Met His Pro Lys Pro His Asp His
                420                 425                 430

Ile Pro Leu Pro Arg Pro Gln Ser Ala Ala Pro Glu Thr Asp Val Pro
                435                 440                 445

Val Asp Thr Asn Leu Ile Glu Phe Asp Thr Asn Tyr Ala Thr Asp Asp
                450                 455                 460

Asp Ile Val Phe Glu Asp Phe Ala Arg Leu Arg Leu Lys Gly Met Lys
465                 470                 475                 480

Asp Asp Asp Tyr Asp Asp Gln Leu Cys
                485

<210> SEQ ID NO 6
<211> LENGTH: 1470
<212> TYPE: DNA
```

<213> ORGANISM: Artificial Sequence
<220> FEATURE:
<223> OTHER INFORMATION: Synthetic nucleotide

<400> SEQUENCE: 6

```
atgggcgtga cccctaacat gatcgactac ttcggcagac cctacgaggg aatcgccgtg      60
ttcgacggca agaaaatcac cgtgaccggc accctgtgga acggcaacaa gatcatcgac     120
gagcggctga tcaaccccga cggcagcctg ctgttcagag tgaccatcaa tggcgtgaca     180
ggctggcggc tgtgcgagag aattctggcc ggactcagat ctcggcgagc tctcgactcc     240
atgggggaga acccgggac cagggtcttc aagaaatcga gtcctaactg caagctcacc      300
gtgtacttgg gcaagcggga cttcgtagat cacctggaca agtggacccc tgtagatggc     360
gtggtgcttg tggaccctga ctacctgaag gaccgcaaag tgtttgtgac cctcacctgc     420
gccttccgct atggccgtga agacctggat gtgctgggct gtccttccg caaagacctg      480
ttcatcgcca cctaccaggc cttccccccg gtgcccaacc caccccggcc cccacccgc      540
ctgcaggacc ggctgctgag gaagctgggc agcatgccc accccttctt cttcaccata     600
ccccagaatc ttccatgctc cgtcacactg cagccaggcc agaggatac aggaaaggcc      660
tgcggcgtag actttgagat tcgagccttc tgtgctaaat cactagaaga gaaagccac     720
aaaaggaact ctgtgcggct ggtgatccga aggtgcagt tcgccccgga gaaacccggc     780
ccccagcctt cagccgaaac acacgccac ttcctcatgt ctgaccggtc cctgcacctc      840
gaggcttccc tggacaagga gctgtactac catggggagc ccctcaatgt aaatgtccac     900
gtcaccaaca actccaccaa gaccgtcaag aagatcaaag tctctgtgag acagtacgcc     960
gacatctgcc tcttcagcac cgcccagtac aagtgtcctg tggctcaact cgaacaagat    1020
gaccaggtat ctcccagctc cacattctgt aaggtgtaca ccataacccc actgctcagt    1080
gacaaccggg agaagcgggg tctcgccctg gatgggaaac tcaagcacga ggacaccaac    1140
ctggcttcca gcaccatcgt gaaggagggt gccaacaagg aggtgctggg aatcctggtg    1200
tcctacaggg tcaaggtgaa gctggtggtg tctcgaggcg gggatgtctc tgtggagctg    1260
ccttttgttc ttatgcaccc caagcccac gaccacatcc ccctccccag accccagtca    1320
gccgctccgg agacagatgt ccctgtggac accaacctca ttgaatttga taccaactat    1380
gccacagatg atgacattgt gtttgaggac tttgcccggc ttcggctgaa ggggatgaag    1440
gatgacgact atgatgatca actctgctaa                                      1470
```

<210> SEQ ID NO 7
<211> LENGTH: 150
<212> TYPE: PRT
<213> ORGANISM: Artificial Sequence
<220> FEATURE:
<223> OTHER INFORMATION: Synthetic construct

<400> SEQUENCE: 7

```
Met Leu Cys Cys Leu Arg Arg Thr Lys Gln Val Glu Lys Asn Asp Glu
1               5                   10                  15

Asp Gln Lys Ile Met Val Ser Lys Gly Gly Gly Gly Ser Gly Gly Gly
            20                  25                  30

Gly Ser Gly Gly Gly Ser Gly Gly Glu Leu Arg Gly Gly Glu Leu Glu
        35                  40                  45

Met Val Phe Thr Leu Glu Asp Phe Val Gly Asp Trp Arg Gln Thr Ala
    50                  55                  60

Gly Tyr Asn Leu Asp Gln Val Leu Glu Gln Gly Gly Val Ser Ser Leu
```

```
                      65                  70                  75                  80
Phe Gln Asn Leu Gly Val Ser Val Thr Pro Ile Gln Arg Ile Val Leu
                85                  90                  95

Ser Gly Glu Asn Gly Leu Lys Ile Asp Ile His Val Ile Ile Pro Tyr
            100                 105                 110

Glu Gly Leu Ser Gly Asp Gln Met Gly Gln Ile Glu Lys Ile Phe Lys
        115                 120                 125

Val Val Tyr Pro Val Asp Asp His His Phe Lys Val Ile Leu His Tyr
    130                 135                 140

Gly Thr Leu Val Ile Asp
145                 150

<210> SEQ ID NO 8
<211> LENGTH: 450
<212> TYPE: DNA
<213> ORGANISM: Artificial Sequence
<220> FEATURE:
<223> OTHER INFORMATION: Synthetic nucleotide

<400> SEQUENCE: 8
atgtgctgtc tgagaagaac caaacaggtt gaaaagaatg atgaggacca aaagatcatg          60
gtgagcaagg gcggcggagg ttccggtggg ggtggctctg gcggaggttc cggtggagag         120
ctccgcggtg gagagctcga gatggtgttc accctggaag atttcgtggg cgactggcgg         180
cagaccgccg gctacaatct ggaccaggtg ctggaacagg gcggcgtgtc cagcctgttt         240
cagaacctgg gcgtgtccgt gacccccatc cagagaatcg tgctgagcgg cgagaacggc         300
ctgaagatcg acatccacgt gatcatccct tacgagggcc tgtccggcga ccagatgggc         360
cagatcgaga agatctttaa ggtggtgtac cccgtggacg accaccactt caaagtgatc         420
ctgcactacg gcaccctcgt gatcgactaa                                           450
```

ASSAYS USING ARRESTIN RECRUITMENT AND UNMODIFIED RECEPTORS

This invention was made with government support under 5R01MH054137, awarded by NIMH. The government has certain rights in this invention.

FIELD OF THE INVENTION

The current invention is in the field of assays, specifically assays that detect or measure the activation and/or inhibition, i.e., modification, of receptors, without modifying the receptor with a label or tag, using the recruitment of arrestin. The current invention uses polypeptides generated from a unique cleavage of a modified *Oplophorus* luciferase.

BACKGROUND OF THE INVENTION

G protein-coupled receptors (GPCRs) are membrane proteins that transmit signals from outside the cell to the cytoplasm. G protein-coupled receptors are found only in eukaryotes, including yeast, and animals. The ligands that bind and activate these receptors include light-sensitive compounds, odors, pheromones, hormones, and neurotransmitters, and vary in size from small molecules to peptides to large proteins. G protein-coupled receptors are involved in many diseases and are also the target of at least 25% of all modern medicinal drugs.

The signaling of many GPCRs by diverse agonists is thought to be terminated by a two-step mechanism (Freedman and Lefkowitz (1996) *Recent Prog Horn Res*. 51:319-51). In this model, the activated receptor is phosphorylated first by a G protein-coupled receptor kinase (GRK), and then an arrestin protein binds to the activated receptor. This arrestin-receptor complex blocks further G protein-receptor interaction and is subsequently internalized. The receptor is then either dephosphorylated or degraded. Recent evidence suggests that the receptor can continue to signal to various effectors after internalization from various intracellular locations, including endosomes. Thus, the recruitment, and subsequent binding, of arrestin to the GPCR can not only read out on the process of receptor activation, but also critically modulate receptor activation and localization.

In addition, arrestins, once recruited to GPCRs, have been shown to signal independently of G proteins. In order to develop drugs with increased efficacy and improved side effect profiles, significant efforts have gone towards the discovery of drugs that selectively activate either G proteins or arrestins.

High throughput assays are available on the market that measure either the activation of G proteins or recruitment of arrestins to GPCRs in a drug-dependent manner. However, all of these assays require the labeling of the arrestin and the GPCR, thus modifying the receptor. This modification can lead to artificial results, such as artificially augmenting or inhibiting a drug's pharmacological activity at the modified receptor. Furthermore, some receptors are not readily labeled at their C-terminus, thus precluding their study in such an assay design.

Thus, there is a need in the industry for an assay that measures a test compound's effect on a GPCR without modifying the receptor. This same need would exist with regard to other cellular receptors, including other membrane bound receptors, located on the plasma membrane or on membranes of intracellular organelles, at which ligand binding or a change in post-translational modification leads to recruitment of another protein.

SUMMARY OF THE INVENTION

This invention is based upon the discovery that the activation or inhibition of a receptor by agonist or antagonist binding can be detected, identified and/or measured without labeling, tagging or otherwise modifying the receptor, by detecting and/or measuring the movement, translocation, recruitment, and/or binding of a first protein to the receptor, when the receptor is activated or inhibited or otherwise modified. The detection and/or measurement of the first protein is accomplished by attaching or conjugating a label or tag to the first protein. However, rather than label or tag the receptor directly, a second protein that is in the same compartment or co-resident or in proximity with the receptor of interest, is conjugated with a label or tag that is complementary to the first protein, such that when the two proteins come in proximity, the labels or tags interact to generate a detectable and/or measurable signal. This is an advantage in drug screening where the modification of a receptor by tags or labels, could alter the receptor's structure and function. This in turn can lead to false readings regarding a test agent's activity as an agonist or antagonist of the receptor.

This invention is also based upon the discovery that the use of two luminescent polypeptides that comprise the amino acid sequences of SEQ ID NOs: 1 and 2, as the labels or tags in the methods and assays of the invention yields superior results.

Thus, one embodiment of the current invention is a method of screening for and/or identifying an agonist, antagonist or allosteric modulator of a receptor, comprising:
  a. fusing, linking, conjugating or attaching a first polypeptide comprising the amino acid sequence of SEQ ID NO: 2 to a first protein, wherein the first protein is known to move, translocate, be recruited, and/or bind to the receptor upon modification of the receptor;
  b. fusing, linking, conjugating or attaching a second polypeptide comprising the amino acid sequence of SEQ ID NO: 1 to a second protein, wherein the second protein is in proximity to and/or in the same compartment as the receptor, and the second polypeptide is capable of interacting with the first polypeptide used in step (a), to generate a detectable and/or measurable signal;
  c. contacting a test agent with the receptor; and
  d. detecting and/or measuring the signal generated by the interaction of the first polypeptide with the second polypeptide;

wherein if a signal is detected and/or measured in step (d), the test agent has bound to the receptor and is identified as an agonist, antagonist or allosteric modulator of the receptor.

Another embodiment is a method of identifying a modification of a receptor, comprising:
  a. fusing, linking, conjugating or attaching a first polypeptide comprising the amino acid sequence of SEQ ID NO: 2 to a first protein, wherein the first protein is known to move, translocate, be recruited, and/or bind to the receptor upon modification of the receptor;
  b. fusing, linking, conjugating or attaching a second polypeptide comprising the amino acid sequence of SEQ ID NO: 1 to a second protein, wherein the second protein is in proximity to and/or in the same compartment as the receptor, and the second polypeptide is capable of interacting with the first polypeptide used in step (a), to generate a detectable and/or measurable signal;

c. contacting a test agent with the receptor; and d. detecting and/or measuring the signal generated by the interaction of the first polypeptide with the second polypeptide;

wherein if a signal is detected and/or measured in step (d), the test agent has modified the receptor.

In some embodiments, the modification of the receptor is activation and the test agent is identified as an agonist.

In some embodiments, the modification of the receptor is inhibition and the test agent is identified as an antagonist.

A further embodiment is an assay for screening for and/or identifying an agonist, an antagonist or an allosteric modulator of a receptor, comprising:

a. a first polypeptide comprising the amino acid sequence of SEQ ID NO: 2 fused, linked, conjugated or attached to a first protein, wherein the first protein is known to move, translocate, be recruited, and/or bind to the receptor upon modification of the receptor;

b. a second polypeptide comprising the amino acid sequence of SEQ ID NO: 1 fused, linked, conjugated or attached to a second protein, wherein the second protein is in proximity to and/or in the same compartment as the receptor, and the second polypeptide is capable of interacting with the first polypeptide, to generate a detectable and/or measurable signal;

c. a test agent, wherein the test agent is being screened or identified as an agonist or antagonist of the receptor; and d. a substrate for *Oplophorus* luciferase;

wherein if the test agent activates or inhibits the receptor such that the first protein moves or translocates to the receptor in proximity of the second protein, the first and second polypeptide will combine and with the addition of the substrate, produce a luminescent signal, identifying the test agent as an agonist, antagonist or allosteric modulator of the receptor.

Another embodiment is an assay for identifying a modification of a receptor, comprising:

a. a first polypeptide comprising the amino acid sequence of SEQ ID NO: 2 fused, linked, conjugated or attached to a first protein, wherein the first protein is known to move, translocate, be recruited, and/or bind to the receptor upon modification of the receptor;

b. a second polypeptide comprising the amino acid sequence of SEQ ID NO: 1 fused, linked, conjugated or attached to a second protein, wherein the second protein is in proximity to and/or in the same compartment as the receptor, and the second polypeptide is capable of interacting with the first polypeptide, to generate a detectable and/or measurable signal;

c. a test agent, wherein the test agent is being screened or identified as an agonist or antagonist of the receptor; and d. a substrate for *Oplophorus* luciferase;

wherein if the test agent modifies the receptor such that the first protein moves or translocates to the receptor in proximity of the second protein, the first and second polypeptide will combine and with the addition of the substrate, produce a luminescent signal, identifying the test agent as an agonist or antagonist of the receptor.

In some embodiments, the modification of the receptor is activation.

In some embodiments, the modification of the receptor is inhibition.

Because of the advantage of screening for ligands at an unmodified receptor, this assay and method can be used on any receptor that is of interest. These receptors would include all cellular receptors including G protein-coupled receptors (GPCRs), enzyme linked receptors, channel-linked receptors, and intracellular receptors. Because hundreds of G protein-coupled receptors have been identified and because GPCRs are an attractive target for drug development, these types of receptors are the target in one embodiment of the invention.

The first protein that is labeled or tagged in the method or assay is any protein known to move, translocate, be recruited, and/or bind to the receptor of interest when the receptor is modified. One embodiment of the invention uses arrestin, which is known to translocate from the cytoplasm to GPCRs when an agonist binds to the receptor. Other proteins that can be used when a GPCR is of interest are G protein coupled receptor kinases (GRKs). While there are hundreds of GPCRs, there are about ten total arrestin and GRK proteins. Other proteins would be used depending upon the receptor of interest and would be well within skill of the art to choose an appropriate protein.

The second protein used in the methods and assays of the invention is an unrelated marker protein or other protein which is in close proximity to and/or in the same compartment as the receptor of interest. For receptors found in the plasma membrane, this protein could be a plasma membrane protein, such as fragment of GAP43 that is doubly palmitoylated. Other plasma membrane proteins can be used and would include but is not limited to fragments of KRas or HRas. For intracellular receptors, markers on the organelles where the receptor is found would be used. These would include but are not limited to protein-tyrosine phosphatase (endoplasmic reticulum), giantin, (Golgi), Rab5 and 11 (endosome), Rab7 (endosome and lysosome), MoA (monoamine oxidase on the outer mitochondrial membrane), ABC (mitochondrial matrix), and IMS (mitochondrial intermembrane space).

The first and second polypeptides used to tag the first and second proteins comprise the amino acid sequences in SEQ ID NOs: 1 and 2. These two polypeptides are the result of a unique cleavage in the polypeptide that comprises a modified *Oplophorus* luciferase, which results in two unique polypeptides that have been found to have enhanced luciferase when recombined in the methods and assays of the current invention.

Additionally, the polynucleotide encoding SEQ ID NOs: 1 and 2, which comprise the nucleotide sequences SEQ ID NOs: 3 and 4, respectively, comprise codon optimization for the polypeptides enhanced luciferase.

Because the methods and assays of the invention can be performed without modifying the receptor of interest, they can also be used in methods and assays that determine the pharmacokinetic properties of drugs, such as binding coefficients, identification of ligands of so-called orphan receptors, evaluation of closely related agents for receptor binding, and determining compound selectivity by screening one compound against a number of receptor variants or mutants.

The current invention also includes compositions, vectors, cells, cell lines, systems, and kits that can be used to perform the methods and assays of the invention, in particular, in a high throughput screening format.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For the purpose of illustrating the invention, certain embodiments of the invention are depicted in drawings. However, the invention is not limited to the precise arrangements and instrumentalities of the embodiments depicted in the drawings.

FIG. 1 are graphs showing that the luminescent polypeptides D1 and D2 do not produce luminescence individually but do form a fully functional protein when placed in proximity. FIG. 1A shows the D1 and D2 polypeptides do not produce luminescence over background. FIG. 1B shows that when D1 and D2 are placed in proximity, a fully functional luminescent protein is formed.

FIG. 2 show the nucleotide sequence (SEQ ID NO: 6) and amino acid sequence (SEQ ID NO: 5) of the construct D2-linker-arrestin3. D2 is shown in red text, the linker in black, and the arrestin3 in green. FIG. 2 also shows the nucleotide sequence (SEQ ID NO: 8) and the amino acid sequence (SEQ ID NO: 7) of the construct membrane marker-linker-D1. D1 is shown in blue text, the linker in black, and the membrane marker in tan.

DETAILED DESCRIPTION OF THE INVENTION

Definitions

Figure 3:
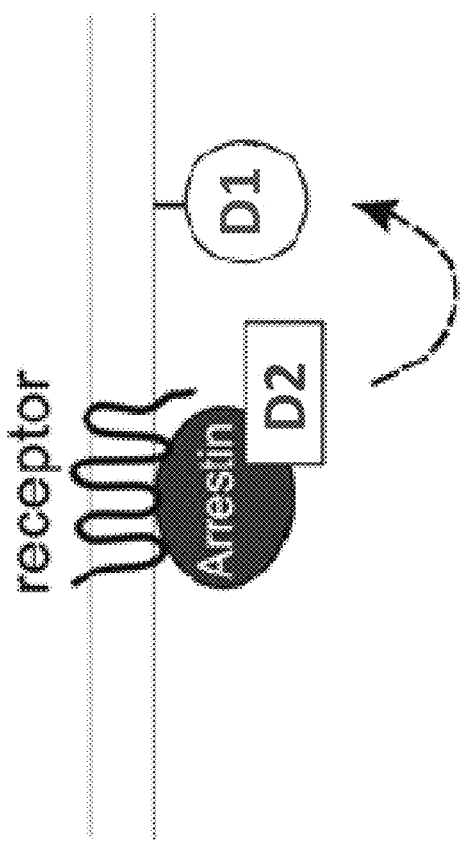
FIG. 3 is a schematic of the arrestin recruitment assay using luciferase polypeptides D1 and D2.

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "agent" as used herein means a substance that produces or is capable of producing an effect and would include, but is not limited to, chemicals, pharmaceuticals, biologics, small organic molecules, antibodies, nucleic acids, peptides, and proteins.

The term "test agent" would be an agent as defined above, which can be tested for its ability to produce an effect. In some embodiments of the current invention, the test agent is tested for its ability to bind to, or otherwise agonize or activate or otherwise modify a receptor or other protein of interest.

The terms "screen" and "screening" and the like as used herein means to test an agent to detect and/or determine if it has a particular action or efficacy.

The terms "identification", "identify", "identifying" and the like as used herein means to test an agent and detect and/or determine if it has a particular action or efficacy.

An "agonist" is defined herein as a compound that interacts with (e.g., binds to) a protein, and promotes, enhances, stimulates or potentiates the biological expression or function of the protein. An "antagonist" interacts with (e.g., binds to) and inhibits or reduces the biological expression or function of the protein.

"Luminescence" as used herein refers to the light output of the luciferase polypeptide under appropriate conditions, e.g. in the presence of a suitable substrate. The light output may be measured as an instantaneous or near-instantaneous measure of light output (which is sometimes referred to as "T=0" luminescence or "flash") upon start of the luminescence reaction, which may start upon addition of a substrate. The light output or luminescence may also be measured over time for a period of for example seconds, minutes, and hours. The light output or luminescence may be reported as the average over time, the half-life of decay of signal, the sum of the signal over a period of time, or as the peak output.

Enhanced luminescence, as used herein, may include any of the following: increased light emission, altered kinetics of light emission, e.g., greater stability of the light intensity, or altered luminescence color, e.g., a shift towards shorter or longer wavelengths.

As used herein wild type "Oplophorus luciferase" is a complex of native 35 kDa and 19 kDa proteins. The 19 kDa protein is the smallest catalytic component (GenBank accession BAB13776, 196 amino acids). The current invention uses two unique polypeptides and their variants generated from a modified Oplophorus luciferase.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include, but are not limited to, plasmids, phages, and viruses.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes and may be from the same or different organisms. A large number of vectors, including plasmid and fungal vectors, have been described for replication and/or expression in a variety of eukaryotic and prokaryotic hosts, and many appropriate host cells, are known to those skilled in the relevant art. Recombinant cloning vectors will often include one or more replication systems for cloning or expression, one or more markers for selection in the host, e.g. antibiotic resistance, and one or more expression cassettes.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described herein.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates) and with charged linkages (e.g., phosphorothioates, phosphorodithioates). Polynucleotides may contain one or more additional covalently linked moieties, such as, for example, proteins (e.g., nucleases, toxins, antibodies, signal peptides, poly-L-lysine), intercalators (e.g., acridine, psoralen), chelators (e.g., metals, radioactive metals, iron, oxidative metals), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin. Sequence identity can be determined using any of a number of publicly available sequence comparison algorithms, such as BLAST, FASTA, DNA Strider, or GCG (Genetics Computer Group, Program Manual for the GCG Package, Version 7, Madison, Wis.).

The term "amino acid," includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, alpha-methylalanine, para-benzoylphenylalanine, phenylglycine, propargylglycine, sarcosine, and tert-butylglycine). The term also includes natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide).

The terms "peptide" and "polypeptide" includes any sequence of two or more amino acids. Peptide sequences specifically recited herein are written with the amino terminus on the left and the carboxy terminus on the left.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Assays and Methods of the Invention

The advantage of the methods and assays of the current invention is that agonists and antagonists of receptors can be screened for, identified, and further tested for binding selectivity, specificity, pharmacokinetic properties, and the like without modifying the structure and function of the receptor. This means that the results obtained from the methods and assays of the current invention are more accurate with regard to ligand and agonist or antagonist binding and function vis a vis the receptor.

There are two types of binding sites for receptors including GPCRs. Orthosteric binding sites are natural active binding sites of a receptor, i.e., the binding site of the endogenous ligand, and allosteric sites are found on other sites on the protein. Ligands can act at the orthosteric site to fully activate a receptor, and are full agonists, or partially activate a receptor and are partial agonists, or fully inhibit basal activity of a receptor and are full inverse agonists, or partially inhibit basal activity of a receptor and are partial inverse agonists, or simply compete at the binding site without changing activity and are neutral antagonists. Allosteric ligands also can activate, or inhibit the receptor, either fully or partially, either on their own, or by enhancing the ability of agonists or inverse agonists that bind in the orthosteric stie. The methods and assays of the current invention can be used to screen for and identify agonists, inverse agonists, neutral antagonists as well as positive or negative allosteric modulators.

The methods and assays of the invention use the interaction between a protein, that moves, translocates, is recruited and/or binds to a receptor upon modification of the receptor, i.e., a first protein, and an unrelated protein that is in the same compartment and/or in proximity to the receptor, i.e., a second protein, or the interaction of the labels or tags linked, conjugated or attached to the first and second proteins. The interaction between the first and second protein, or the tags or labels is detected by any method known in the art used for the detection.

In the particular embodiment of the invention, the first protein is fused, linked, conjugated or attached to a first polypeptide comprising the amino acid sequence SEQ ID NO: 2 and the second protein is fused, linked, conjugated or attached to a second polypeptide comprising the amino acid sequence SEQ ID NO: 1.

When the first protein moves, is translocated, recruited and/or binds to the receptor of interest in response to the modification, i.e., activation or inhibition, of the receptor by a test agent, the first polypeptide, SEQ ID NO: 2, comes into proximity with the second polypeptide, SEQ ID NO: 1, which is fused, linked, conjugated or attached to the second protein, which is in proximity to and/or in the same compartment as the receptor of interest. The first polypeptide and second polypeptide combine to form a modified *Oplophorus* luciferase. Upon addition of an appropriate substrate, detectable luminescence is produced.

Thus the general method of the invention for screening for and/or identifying an agonist or antagonist or an allosteric modulator of a receptor, comprises: providing a first protein fused, linked, conjugated or attached to a first polypeptide comprising the amino acid sequence SEQ ID NO: 2, wherein the first protein moves, translocates, is recruited and/or binds to a receptor upon modification, e.g., activation or inhibition, of the receptor; providing a second protein fused, linked, conjugated or attached to a second polypeptide comprising the amino acid sequence SEQ ID NO: 1, wherein the second protein is in proximity to and/or in the same compartment as the receptor of interest; providing a test agent, wherein the test agent is being screened or identified as an agonist or antagonist or an allosteric modulator of the receptor; and providing a substrate for *Oplophorus* luciferase. If the test agent activates the receptor such that the first protein moves or translocates to the receptor in proximity of the second protein, the first and second polypeptide will combine and with the addition of the substrate, produce a luminescent signal.

One advantage of the current invention is that helper peptides such as SH3 and Sp1 are not needed to obtain superior results. While a previous application of a related method required helper peptides to increase the affinity between arrestin and the second protein for optimal resonance energy transfer (Donthamsetti et al. (2015) *Curr. Prot. Pharmacol.* 70:2.14.1-2.14.14), the current invention using the luciferase polypeptides does not require the helper peptides, which could in theory artificially enhance recruitment and provide a bias in the output. The absence of helper peptides ensures that the only interaction between the first protein and the second protein is that mediated by recruitment of the first protein to the proximity of the second protein by the activated receptor itself. It also results in a more streamlined assay.

The method of the invention can also include an "enhancing agent" for use in enhancing the interaction, especially when a GPCR is the receptor of interest, and arrestin, the first protein. One such enhancing agent is a G protein coupled receptor kinase (GRK). The GRK can be added to the assay or method by the co-transfection of a construct overexpressing a GRK. It should be noted that while a GRK can be included in the methods and assays of the invention, one advantage of the current invention is that it is not required. All of the exemplified assays worked as expected without the use of GRKs. This is an improvement over other methods and assays which utilize arrestin.

The method of the invention exemplified below used an expression vector comprising a first protein, arrestin3, linked to D2 (SEQ ID NO: 2) (FIG. 2, SEQ ID NOs: 5 and 6) and a membrane bound second protein linked to D1 (SEQ ID NO: 1) (FIG. 2, SEQ ID NOs: 7 and 8). Cells comprising various GPCRs including β2-adrenergic receptor (B2R), dopamine 2 receptor (D2R), μ opioid receptor (MOR), κ opioid receptor (KOR), Nociceptin opioid receptor (NOR), vasopressin receptor 1 (V1A), cannabinoid receptor 1 (CB1) and cannabinoid receptor 2 (CB2) were transfected with this expression vector and the results showed that when the proper ligand and substrate were added to the cells, the binding of the ligand to the receptor could be detected via luminescence (Examples 3 and 4).

It will be appreciated by those of skill in the art that the methods of the invention can be performed using various compositions, systems, cells, cell lines, and the like which are described herein.

As will be discussed below, the methods and assays of the current invention can be expanded for use with other receptors, and other first and second proteins.

Receptors and Proteins Known to Move, Translocate, be Recruited, and/or Bind to the Activated Receptor (First Proteins)

In the exemplified embodiments, the test agent is a ligand of a GPCR, including β2-adrenergic receptor (B2R), dopamine 2 receptor (D2R), μ opioid receptor (MOR), κ opioid receptor (KOR), δ opoid receptor (DOR), Nociceptin opioid receptor (NOR), vasopressin receptor 1 (V1A), cannabinoid receptor 1 (CB1) and cannabinoid receptor 2 (CB2) and the labeled first protein is arrestin3. However, other receptors can be the targets of the methods of the invention, including other cell surface receptors and intracellular receptors. The method and assays of the invention can also be used to monitor the movement of proteins within a cell from organelle to organelle.

GPCRs are the largest family of cell-surface receptors and are found in all eukaryotes. Hundreds of different G-protein-linked receptors have been identified. Well-known examples include the β-adrenergic receptor, the muscarinic-type acetylcholine receptors, metabotropic glutamate receptors, receptors for odorants in the olfactory system, and many types of receptors for peptide hormones. Rhodopsin, a light-sensitive 7-transmembrane protein in retinal photoreceptors, is another type of GPCR. GPCRs mediate the responses to an enormous diversity of signal molecules, including hormones, neurotransmitters, and local mediators. The same ligand can activate many different receptor family members. GPCRs are involved in vision, taste, smell, behavioral and mood regulation, regulation of the immune system, and the autonomic nervous system. There are also orphan GPCRs that have no identified ligand. While nine different GPCRs are exemplified, any of the other GPCRs can be used in the current assays and methods.

All GPCRs have similar overall structure in the transmembrane domain, consisting of a single polypeptide chain threading back and forth the lipid bilayer seven times. When extracellular signaling molecules bind to GPCRs, the receptors undergo a conformational change that enables them to activate trimeric GTP-binding proteins (G proteins). These G proteins are attached to the cytoplasmic face of the plasma membrane, where they serve as relay molecules, functionally coupling the receptors to enzymes or ion channels in this membrane. G proteins are composed of three subunits, Gα, Gβ, and Gγ. In an unstimulated state, the Gα subunit is GDP bound and the G protein is inactive. When stimulated by the activated GPCR, the Gα subunit releases its bound GDP, allowing GTP to bind in its place. The trimer becomes two signaling proteins—the Gα subunit and the Gβγ complex.

Termination, as discussed above, is mediated by a G protein coupled receptor kinase (GRK) and arrestin. While there are a vast number of GPCRs, there are only six GRKs and four arrestins, arrestin-1, arrestin-2, arrestin-3, and arrestin-4. Since these proteins are recruited and move to the GPCR at activation of the receptor, they can be labeled for detection with, for example, SEQ ID NO: 2 or variants thereof.

Arrestin3 fused to SEQ ID NO: 2 is exemplified, but any of the other three arrestins can be used and it will be within the skill of the art to choose the appropriate one for the G protein-coupled receptor of interest.

Alternatively, one of the six GRKs can be labeled for detection with SEQ ID NO: 2 or variants thereof if desired.

Other receptors for which there is a need to test for drugs without modifying the receptor include enzyme-linked receptors, which are the second major cell-surface receptor. They were recognized initially through their role in responses to extracellular signal proteins that promote the growth, proliferation, differentiation, or survival of cells in animal tissues. These signal proteins are often collectively called growth factors, and they usually act as local mediators at very low concentrations (about $10^{-9}$-$10^{-11}$ M). Disorders of cell proliferation, differentiation, survival, and migration are fundamental events that can give rise to cancer, and abnormalities of signaling through these receptors have major roles in this class of disease.

Six classes of enzyme-linked receptors have thus far been identified: receptor tyrosine kinases; tyrosine kinase associated receptors; receptor like tyrosine phosphatases; receptor serine/threonine kinases; receptor guanylyl cyclases; and histadine-kinase associated receptors.

Any protein that is moves, translocates, is recruited, and/or binds to these receptors when the receptor is activated by a ligand or agonist, can be fused to polypeptide SEQ ID NO: 2 or variants thereof.

For example, many proteins bind to activated receptor tyrosine kinases including enzymes such as phospholipase C-γ. While these proteins are varied, they usually have a highly conserved SH2 or PTB domain. These proteins, which are recruited and move to the activated tyrosine kinase receptor, could be used in the assays and methods of the invention. Further examples are the proteins from the Smad family that bind to the type 1 receptor serine/threonine kinase.

Channel-linked receptors, and intracellular receptors can also be targets of the methods and assays, and proteins that move, translocate, are recruited, and/or bind to these receptors can be used.

Additionally, the assay and method can be used to monitor and identify movement of proteins to and from other portions and organelles of the cell, for example, from the cytoplasm to endoplasmic reticulum. For example, a number of cytoplasmic proteins have been shown to be recruited to COPII, a critical ER complex (Malhotra and Erlmann (2011) *EMBO* 30:3475-80).

Unrelated Marker Proteins (Second Protein)

The second proteins used in the methods and assays of the invention are any unrelated protein in proximity to and/or the same compartment as the receptor of interest. This second protein would be labeled or tagged in such a way that its interaction with the first protein can be detected, for example, by fusing it to the polypeptide of SEQ ID NO:1 or variants thereof.

This unrelated marker protein or second protein would be one that does not normally interact with the first protein that would be translocating to, moving towards or binding to the receptor. This unrelated marker protein should also be in proximity of the receptor of interest.

If the receptor is a plasma membrane bound receptor, then the unrelated marker protein should be on the plasma membrane. One example is GAP43. Other plasma membrane markers would include but are not limited to KRas, HRas, and CD8. If the receptor is intracellular, then unrelated marker proteins would include but is not limited to protein-tyrosine phosphatase (endoplasmic reticulum), giantin (Golgi), Rab5 and 11 (endosome), Rab7 (endosome and lysosome), MoA (monoamine oxidase on the outer mitochondrial membrane), ABC (mitochondrial matrix), and IMS (mitochondrial intermembrane space).

If the movement of a protein from one portion of the cell to another is being monitored, then the unrelated marker protein would be found in the organelle to which the protein would move.

The Use of Unique Luminescent Polypeptides as a Means for Detection

The inventors have extensive experience using a bioluminescence resonance energy transfer (BRET)-based method to study arrestin recruitment to the surface by activation of unmodified receptors (Donthamsetti et al. (2015) *Curr. Prot. Pharmacol.* 70:2.14.1-2.14.14). The current invention is based upon the replacement of BRET by the complementation of a unique split modified luciferase protein to create a superior assay to measure arrestin recruitment by measuring luminescence. This unique specific cleavage results in two polypeptides which are ideally suited for use in the methods and assays of the invention.

The luciferase used originates from the deep-sea shrimp *Oplophorus gracilirostris*. The cDNA sequence was codon optimized for expression in mammalian cell lines in total changing 87 basepairs within both SEQ ID NOs: 3 and 4 to create two polypeptides, the N-terminal part 1-102 amino acid (FIG. 2—D1 in blue, SEQ ID NO: 1) and the C-terminal part 103-172 (FIG. 3—D2 in red, SEQ ID NO: 2) (Example 2).

To assess the luminescent polypeptide's ability to form the fully functional luminescent protein, D1 was fused to FKBP (FK506-binding protein) and D2 to FRB (binding domain of the FKBP12-rapamycin-associated-protein). As shown in Example 1 and FIG. 1, this resulted in an 8-fold increase in luminescence.

The luminescent polypeptides were then used in place of the BRET acceptor (citrine attached to the membrane) and donor (Rluc8 on the N-terminal of arrestin3) in an arrestin recruitment assay. The helper peptides SH3 and Sp1 were removed as well. The N-terminal D1 polypeptide (SEQ ID NO: 1) was attached to the membrane and the C-terminal D2 polypeptide (SEQ ID NO: 2) was attached to the N-terminal part of arrestin3 (Example 2, FIG. 2).

When arrestin is recruited to the membrane by agonist-induced receptor activation, the two polypeptides (D1 and D2) will complement to form the fully functional protein, thereby causing an increase in luminescence, when the luminescent protein oxidizes the substrate. See Examples 3 and 4.

While many enzymes have been shown to complement when brought into proximity, this requires that each of the two components be stable and that the components can fold together to create a functional enzyme, something dependent on the specific sites of cleavage.

Four split variants of the modified luciferase polypeptide were made according to prediction of the split's stability from the crystal structure. Despite the fact that based upon the crystal structure these splits should have all recombined to form a full luciferase polypeptide, only one of the four worked in the assay and methods of the invention. Additionally and unexpectedly, when the two polynucleotides from split D recombined in both the initial testing and the arrestin assay, enhanced luciferase was observed. Thus this split of the luciferase protein is particularly well suited for use in the methods and assays of the invention using arrrestin and a marker protein.

These splits in the nucleotides were as follows: split A: 1-78 bp/438 bp; split B: 129 bp/387 bp; split C: 156 bp/360 bp; and split D: 306 bp/210 bp. Splits C and D worked successfully in the initial testing with rapamycin as exemplified in Example 1, however only split D worked in the arrestin recruitment assay. A published split of the luciferase polypeptide was also tested in the arrestin recruitment assay and was found not functional as well (Dixon et al. ACS Chem. Biol. 2016, 11, 400-408).

The N-terminal fragment of the modified luciferase polypeptide (D1) comprises the following amino acid sequence:

```
                                          (SEQ ID NO: 1)
MVFTLEDFVGDWRQTAGYNLDQVLEQGGVSSLFQNLGVSVTPIQRIVLSG
ENGLKIDIHVIIPYEGLSGDQMGQIEKIFKVVYPVDDHHFKVILHYGTLV
ID
```

The C-terminal fragment of the modified luciferase polypeptide (D2) comprises the following amino acid sequence;

```
                                          (SEQ ID NO: 2)
GVTPNMIDYFGRPYEGIAVFDGKKITVTGTLWNGNKIIDERLINPDGSLL
FRVTINGVTGWRLCERILA.
```

Additionally, it has been found that certain codons are optimized in producing a luciferase polypeptide with the amino acid sequences of SEQ ID NOs: 1 and 2 for use in the methods, assays, and systems of the invention. The preferred nucleotide sequence for encoding SEQ ID NO: 1 comprises the nucleotide sequence of SEQ ID NO: 3 and for encoding SEQ ID NO: 2 comprises the nucleotide sequence of SEQ ID NO: 4.

In some embodiments, variants of the polypeptide having at least 80% e.g., at least 85%, 90%, 95%, 96%, 97%, 98%, or 99%, but less than 100% amino acid sequence identity to the polypeptide of SEQ ID NO: 1 can be used in the methods, assays, and systems of the invention.

In some embodiments, variants of the polypeptide having at least 80% e.g., at least 85%, 90%, 95%, 96%, 97%, 98%, or 99%, but less than 100% amino acid sequence identity to the polypeptide of SEQ ID NO: 2 can be used in the methods, assays, and systems of the invention.

In some embodiments, variants of the polynucleotide having at least 60% e.g., at least 65%, 70%, 75%, 80%, 85%, 90%, 95%, 96%, 97%, 98%, or 99%, but less than 100% sequence identity to the polynucleotide of SEQ ID NO: 3 can be used in the methods, assays, and systems of the invention.

In some embodiments, variants of the polynucleotide having at least 60% e.g., at least 65%, 70%, 75%, 80%, 85%, 90%, 95%, 96%, 97%, 98%, or 99%, but less than 100% sequence identity to the polynucleotide of SEQ ID NO: 4 can be used in the methods, assays, and systems of the invention.

In some embodiments of the invention, the polypeptides further comprise one or more heterologous amino acid sequences at the N-terminus, C-terminus, or both (a fusion polypeptide such as one with an epitope or fusion tag), which optionally directly or indirectly interact with the protein of interest. In one embodiment, the presence of the heterologous sequence(s) does not substantially alter the luminescence of the modified luciferase.

In some embodiments, a linker connects the luminescent polypeptide and the protein while providing a desired amount of space/distance between the polypeptides. In certain embodiments, a linker provides appropriate attachment chemistry between the luminescent polypeptide and the protein. A linker may also improve the synthetic process of making the luminescent polypeptide and the protein (e.g., allowing them to be synthesized as a single unit, allowing post synthesis connection of the two elements).

In some embodiments, a linker is any suitable chemical moiety capable of linking, connecting, or tethering the luminescent polypeptide and the protein. In some embodiments, a linker is a polymer of one or more repeating or non-repeating monomer units (e.g., nucleic acid, amino acid, carbon-containing polymer, carbon chain). When the luminescent polypeptide and the protein are part of a fusion protein, a linker (when present) is typically an amino acid chain.

A wide variety of linkers may be used. In some embodiments, the linker is a single covalent bond.

By way of example, the first polypeptide comprises a 10 amino acid linker for attachment to the first protein and the second polypeptide comprises a 24 amino acid linker for attachment to the second protein. See FIG. 2, black sequences.

Under appropriate conditions, i.e., when the first polypeptide and the second polypeptide recombine to form a modified luciferase polypeptide, the modified luciferase polypeptide will produce a light output known as luminescence. Other appropriate conditions include for example are the presence of a suitable substrate. Suitable substrates include but are not limited to furimazine, coelenterazine, and bisdeoxycoelenterazine.

Compositions, Systems, Kits, Vectors, Cells, and Cell Lines

The current invention also includes vectors, compositions, systems, kits, cells, and cell lines for performing the methods and assays of the invention that allows for the detection and identification of agents which are agonists and/or antagonists and/or allosteric modulators, and/or activate and/or inhibit and/or modify a receptor without modifying the receptor with a label or a tag.

One embodiment of the current invention is a vector or expression vector comprising a polynucleotide encoding a first protein that moves, translocates, is recruited, and/or binds to a receptor of interest when the receptor is modified, fused, conjugated, attached or linked with a first polynucleotide encoding the polypeptide comprising the sequence of SEQ ID NO: 2 or variants thereof, and a second polynucleotide encoding a second protein that is in proximity to and/or in the same compartment as the receptor, fused, conjugated, attached or linked with a second polynucleotide encoding the polypeptide comprising the sequence of SEQ ID NO: 1 or variants thereof. In one embodiment, the vectors can comprise polynucleotides that encode protein constructs comprising the sequences of SEQ ID NOs: 5 and 7.

A further embodiment of the current invention is a vector or expression vector comprising a polynucleotide encoding a first protein that moves, translocates, is recruited, and/or binds to a receptor of interest when the receptor is modified, fused, conjugated, attached or linked with a first polynucleotide comprising the sequence of SEQ ID NO: 4 or variants thereof, and a second polynucleotide encoding a second protein that is in proximity to and/or in the same compartment as the receptor, fused, conjugated, attached or linked with a second polynucleotide comprising the sequence of SEQ ID NO: 3 or variants thereof. In one embodiment, the vectors can comprise polynucleotides comprising SEQ ID NOs: 6 and 8.

The vectors can further comprise one or more enhancers, a promoter, a transcription termination sequence or a combination thereof.

Another embodiment of the current invention is a composition comprising a first protein that moves, translocates, is recruited, and/or binds to a receptor of interest when the receptor is modified, fused, conjugated, attached or linked with a first polypeptide comprising the amino acid sequence of SEQ ID NO: 2 or variants thereof, and a second protein that is in proximity to and/or in the same compartment as the receptor, fused, conjugated, attached or linked with a second polypeptide comprising the amino acid sequence of SEQ ID NO: 1 or variants thereof. In one embodiment, the proteins can be linked to the polypeptide or variants of SEQ ID NOs: 1 and 2 with amino acid linkers or other linkers. In one embodiment, the composition can comprise protein constructs with the sequence of SEQ ID NOs: 6 and 8. In one embodiment, the composition can further comprise the receptor of interest. In a further embodiment, the receptor of interest can be added later to the composition. In a further embodiment, the composition can comprise another enhancing agent, such as a vector, plasmid or construct overexpressing GRK protein.

Another embodiment of the current invention is a composition comprising a polynucleotide encoding a first protein that moves, translocates, is recruited, and/or binds to a receptor of interest when the receptor is modified, fused, conjugated, attached or linked with a first polynucleotide encoding the polypeptide comprising the sequence of SEQ ID NO: 2 or variants thereof, and a polynucleotide encoding a second protein that is in proximity to and/or in the same compartment as the receptor, fused, conjugated, attached or linked with a second polynucleotide encoding the polypeptide comprising the amino acid sequence of SEQ ID NO: 1 or variants thereof. In one embodiment, the composition can comprise polynucleotide encoding protein constructs with the sequence of SEQ ID NOs: 5 and 7. In one embodiment, the composition can further comprise a polynucleotide encoding the receptor of interest. In a further embodiment, the polynucleotide encoding the receptor of interest can be added later to the composition. In a further embodiment, the composition can comprise another enhancing agent, such as a vector, plasmid or construct overexpressing GRK protein. In some embodiments the first polynucleotide encoding the polypeptide comprising the sequence of SEQ ID NO: 2 or variants thereof comprises SEQ ID NO: 4. In some embodiments the polynucleotide encoding the polypeptide comprising the sequence of SEQ ID NO: 1 or variants thereof comprises SEQ ID NO: 3. In some embodiments the polynucleotide encoding the protein construct comprising the sequence of SEQ ID NO: 5 comprises SEQ ID NO: 6. In some embodiments the polynucleotide encoding the protein construct comprising the sequence of SEQ ID NO: 7 or variants thereof comprises SEQ ID NO: 8.

A preferred form of the composition is a cell.

A further embodiment of the current invention is a composition comprising a vector or expression vector comprising a polynucleotide encoding a first protein that moves, translocates, is recruited, and/or binds to a receptor of interest when the receptor is modified, fused, conjugated, attached or linked with a first polynucleotide comprising the sequence of SEQ ID NO: 4 or variants thereof, and a second polynucleotide encoding a second protein that is in proximity to and/or in the same compartment as the receptor, fused, conjugated, attached or linked with a second polynucleotide comprising the sequence of SEQ ID NO: 3 or variants thereof. In one embodiment, the vectors can comprise polynucleotides comprising SEQ ID NOs: 6 and 8. The vectors can further comprise one or more enhancers, a promoter, a transcription termination sequence or a combination thereof.

The first and second polynucleotides expressing the proteins can be contained in the same or different vectors.

In a further embodiment, the composition can comprise a vector or expression vector comprising another enhancing agent, such as a vector, plasmid or construct overexpressing GRK protein.

The composition can further comprise a vector or expression vector comprising a polynucleotide encoding the receptor of interest.

The vectors described herein can further comprise one or more enhancers, a promoter, a transcription termination sequence or a combination thereof.

Expression vectors that can be used in the present invention are known in the art and include but are not limited to pcDNA3.1. p3XFLAG-CMV, pBI-CMV, pcDNA4, pcDNA5, pcDNA6.2, and pCMV.

The expression of the first and second proteins as well as the receptor may be controlled by any promoter capable of expression in prokaryotic cells or eukaryotic cells including synthetic promoters. Prokaryotic promoters include, but are not limited to, SP6, T7, T5, tac, bla, trp, gal, lac or maltose promoters, including any fragment that has promoter activity. Eukaryotic promoters include, but are not limited to, constitutive promoters, such as viral promoters such as CMV, SV40 and RSV promoters, as well as regulatable promoters, such as an inducible or repressible promoter such as the tet promoter, the hsp70 promoter and a synthetic promoter regulated by CRE, including any fragment that has promoter activity. The expression vectors may be introduced to a cell by any method including, but not limited to, calcium-mediated transformation, electroporation, microinjection, lipofection and the like.

The most preferred embodiment of the invention is a cell based assay wherein the cell or cells express a first protein that moves, translocates, is recruited, and/or binds to a receptor of interest when the receptor is modified, fused, conjugated, attached or linked with a first polypeptide comprising the amino acid sequence of SEQ ID NO: 2 or variants, and a second protein that is in proximity to and/or in the same compartment as the receptor, fused, conjugated, attached or linked with a second polypeptide comprising the amino acid sequence of SEQ ID NO: 1 or variants thereof. In one embodiment, the cells express proteins with the sequence of SEQ ID NOs: 5 and 7. Methods of obtaining cells expressing these proteins are known in the art and described and exemplified herein. Common mammalian cells such as HEK293T, COS-7, and CHO, as well as primary neuronal culture cells can be used. These cells can be transfected with an expression vector or vectors comprising a polynucleotide encoding a first protein that moves, translocates, is recruited, and/or binds to a receptor of interest when the receptor is modified, fused, conjugated, attached or linked with a first polynucleotide comprising the sequence of SEQ ID NO: 4 or variants thereof, and a second polynucleotide encoding a second protein that is in proximity to and/or in the same compartment as the receptor, fused, conjugated, attached or linked with a second polynucleotide comprising the sequence of SEQ ID NO: 3 or variants thereof. In one embodiment, the vectors can comprise polynucleotides with the sequences of SEQ ID NOs: 6 and 8. In a further embodiment, the cells can also express the receptor of interest or the cells can be manipulated later, at the time of the assay, to express the receptor of interest. In a further embodiment, the cells can also express a plasmid or construct overexpressing GRK protein.

The cells can be in the form of a stable cell line expressing first protein that moves, translocates, is recruited, and/or binds to a receptor of interest when the receptor is modified, fused, conjugated, attached or linked with a first polypeptide comprising the amino acid sequence of SEQ ID NO: 2 or variants thereof, and a second protein that is in proximity to and/or in the same compartment as the receptor, fused, conjugated, attached or linked with a second polypeptide comprising the amino acid sequence of SEQ ID NO: 1 or variants thereof. In one embodiment, the cells express proteins with the sequence of SEQ ID NOs: 6 and 8. The cell line can also express the receptor of interest.

In some embodiments, the cells or cell line are frozen. In some embodiments, the cells or cell line are in solution.

The cells or other composition comprising first protein that moves, translocates, is recruited, and/or binds to a receptor of interest when the receptor is modified, fused, conjugated, attached or linked with a first polypeptide comprising the amino acid sequence of SEQ ID NO: 2 or variants thereof, and a second protein that is in proximity to and/or in the same compartment as the receptor, fused, conjugated, attached or linked with a second polypeptide comprising the amino acid sequence of SEQ ID NO: 1 or variants thereof can be contacted or reacted with the receptor of interest and the test agent, as well as other necessary reagents, e.g., substrate, in any reaction vessel suitable for reacting assay components, such as a test tube, a well of a micro-titer plate, a solid surface, a droplet or a chip.

A preferred embodiment is microtiter plates, such as 96 or 384-well plates, each containing the cells comprising first protein that moves, translocates, is recruited, and/or binds to a receptor of interest when the receptor is modified, fused, conjugated, attached or linked with a first polypeptide comprising the amino acid sequence of SEQ ID NO: 2 or variants thereof, and a second protein that is in proximity to and/or in the same compartment as the receptor, fused, conjugated, attached or linked with a second polypeptide comprising the amino acid sequence of SEQ ID NO: 1 or variants thereof. The cells can also be further transfected or manipulated to express the receptor of interest prior to the addition of the cells to the wells. The test agent as well as other necessary reagents, such as substrate, can be added to the wells.

In some embodiment, the cells express proteins with the sequence of SEQ ID NOs: 5 and 7.

In one embodiment of the compositions and cells, the first protein is an arrestin chosen from arrestin-1, arrestin-2, arrestin-3, and arrestin-4, and the second protein is on the plasma membrane. One such marker protein is GAP43. Any GPCR of interest can be added to the composition including but not limited to β2-adrenergic receptor (B2R), dopamine 2 receptor (D2R), δ opioid receptor (DOR), μ opioid receptor (MOR), κ opioid receptor (KOR), Nociceptin opioid receptor (NOR), vasopressin receptor 1 (V1A), cannabinoid receptor 1 (CB1) and cannabinoid receptor 2 (CB2). Additionally, other receptors of interest can be added to the composition.

The components of the assay can also be in a kit format. Such a kit would include vectors or constructs that encode for, or cells that express, the first protein that moves, translocates, is recruited, and/or binds to a receptor of interest when the receptor is modified, fused, conjugated, attached or linked with a first polypeptide comprising the amino acid sequence of SEQ ID NO: 2 or variants thereof, and a second protein that is in proximity to and/or in the same compartment as the receptor, fused, conjugated, attached or linked with a second polypeptide comprising the amino acid sequence of SEQ ID NO: 1, or variants thereof, other reagents for performing the assay, and instructions for use. Other reagents would include microtiter plates, reagents for transfecting the cells with the receptor of interest, substrate for the luciferase reaction, buffers and the like. The vectors and cells can be in solution or in a composition. If the kit comprises cells, the cells can also express the receptor of interest.

In one embodiment, the vectors encode for, or cells express, proteins with the sequence of SEQ ID NOs: 5 and 7. In some embodiments the vectors can comprise polynucleotides comprising the sequences of SEQ ID NOs: 3, 4, 6, and/or 8.

One form of such a kit would be frozen cells comprising the first protein that moves, translocates, is recruited, and/or binds to a receptor of interest when the receptor is modified, fused, conjugated, attached or linked with a first polypeptide comprising the amino acid sequence of SEQ ID NO: 2 or variants thereof, and a second protein that is in proximity to and/or in the same compartment as the receptor, fused, conjugated, attached or linked with a second polypeptide comprising the amino acid sequence of SEQ ID NO: 1 or variants thereof, other reagents for performing the assay and instructions for use. Other reagents would include microtiter plates, reagents for transfecting the cells with the receptor of interest, substrate for the luciferase reaction, buffers and the like. In some embodiments the cells also express the receptor of interest. In one embodiment, the cells express proteins construct with the sequence of SEQ ID NOs: 5 and 7.

A further embodiment of the present invention is a system for performing the methods of the present invention. Such a system can comprise at least vectors or constructs that encode for, or cells that express, the first protein that moves, translocates, is recruited when the receptor is modified and/or binds to a receptor of interest, fused, conjugated, attached or linked with a first polypeptide comprising the amino acid sequence of SEQ ID NO: 2 or variants thereof, and a second protein that is in proximity to and/or in the same compartment as the receptor, fused, conjugated, attached or linked with a second polypeptide comprising the amino acid sequence of SEQ ID NO: 1 or variants thereof. Further components of the system would include at least reagents for transfecting the cells with the receptor of interest, and substrate for the luciferase reaction. If the system comprises cells, the cells can also express the receptor of interest. In one embodiment, the vectors or constructs can encode for, or the cells can express, proteins with the sequence of SEQ ID NOs: 5 and 7. In some embodiments the vectors can comprise polynucleotides comprising the sequences of SEQ ID NOs: 3, 4, 6, and/or 8.

Because the present invention does not require GRK or receptor modification, it is very amenable to in vivo use in animal models. Thus, a further embodiment of the present invention are transgenic animals including but not limited to mice. These animals can be obtained using the cells and gene constructs disclosed herein and then used for in vivo or ex vivo testing of agents using the methods of the invention.

While the use of recombinant technology is exemplified herein, the protein constructs comprising the proteins such as arrestin and membrane markers fused to the luminescent polypeptides can by synthesized using conventional protein synthesis methods.

The methods and assays of the present invention can be automated for convenient high-throughput screening to, for example, test large numbers of test agents for their ability to bind to or otherwise modulate a receptor of interest. Automated methods can be used to detect binding of the labeled assay components. The binding of the assay components can be detected by comparing the assay reaction before and after contact with a test agent or agents, or by comparison to a known control. Both qualitative and quantitative measurements can be made using the methods and assays of the invention using automated techniques known in the art.

Computer programs can be utilized to process samples, record output and/or process data. Such programs are known in the art.

EXAMPLES

The present invention may be better understood by reference to the following non-limiting examples, which are presented in order to more fully illustrate the preferred embodiments of the invention. They should in no way be construed to limit the broad scope of the invention.

Example 1—Generation of Polypeptides with Increased Luminescence

Starting with the sequence for luciferase originating from the deep-sea shrimp *Oplophorus gracilirostris*, the cDNA was codon optimized for expression in mammalian cell lines in total changing 87 basepairs (see SEQ ID NOs: 3 and 4). The cDNA was used to express the N-terminal part of the protein comprising amino acids 1-102 (SEQ ID NO: 1) and the C-terminal part of the protein comprising amino acids 103-172 (SEQ ID NO: 2).

To assess these polypeptides' ability to form the fully functional protein, SEQ ID NO: 1 was fused to FKBP (FK506-binding protein) and SEQ ID NO: 2 was fused to FRB (binding domain of the FKBP12-rapamycin-associated-protein). These will be dimerized efficiently by the macrolide rapamycin. The polypeptides alone did not produce luminescence when compared to background (UT i.e. untransfected cells) (FIG. 1A), whereas transfection with FKBP-D1 and FRB-D2 resulted in an 8-fold increase in luminescence upon rapamycin addition (FIG. 1B).

Example 2—Constructs Comprising Polypeptides with Increased Luminescence

The polypeptides generated in Example 1, SEQ ID NOs: 1 and 2, were used to create an assay to measure arrestin recruitment by measuring luminescence.

The N-terminal SEQ ID NO: 1 (D1) was attached to the membrane, resulting in construct membrane marker-linker D1 (nucleotide sequence shown in SEQ ID NO: 8 and amino acid sequence shown in SEQ ID NO: 7) and the C-terminal SEQ ID NO: 2 (D2) was attached to the N-terminal part of arrestin3, resulting in constructs D2-linker-arrestin (nucleotide sequence shown in SEQ ID NO: 6 and amino acid sequence shown in SEQ ID NO: 5) (FIG. 2).

When arrestin is recruited to the membrane by agonist-induced receptor activation, the luminescent polypeptides will complement to form the fully functional protein, thereby causing an increase in luminescence, when the full luciferase polypeptide oxidizes the substrate (FIG. 3).

Example 3—Testing of Constructs to Identify Ligands of GPCRs

The constructs described in Example 2 were cloned into pcDNA3.1+ vectors and tested by transfection into HEK293 cells using the following protocols.

Materials
Hek293 cells
Cell growth media: DMEM, pen/strep, FBS
Trypsin
Transfection agent polyethyleimine (PEI 1 µg/ul)
Mammalian expression plasmids containing: mem-linker-D1, D2-linker-Arrestin3, receptor and GRK2/6 (optional)
coelenterazine H
Pherastar or other machine to measure luminescence
DPBS
Glucose
10 cm$^2$ tissue culture plates
White 96-well flat bottom plate or Black/White 96-well Isoplate
Methods
Day 1:
Seed Hek293 Cells:
  Aspirated media from a 10-cm plate, washed with DPBS, added 2 ml trypsin/flask, and spun down 3 min 0.6 rcf 10 cm$^2$ plate: 4*10$^6$ cells (volume: 10 ml)
Day 2:
Transfection:
  DNA mix was prepared for each transfection with the plasmids containing mem-D1 (SEQ ID NO: 8), Arrestin3-D2 (SEQ ID NO: 6), receptor of interest and optionally GRK2/6. The total DNA amount was 10 µg and was adjusted with the addition of empty vector i.e., pcDNA3.1+.
  The transfection was carried out using 1 µg receptor, 0.5 µg mem-D1 and D2-Arrestin3, 3.2 µg GRK2, and 5.8 µg pcDNA3.1+.
  1 ml DMEM was added to the DNA mix and PEI at a 1:1 ratio i.e. 10 µl was added to DNA and vortexed—was let to stand for 15 min and added drop wise to the cells (to avoid detachment).
Day 3:
Changed media
Day 4:
Assay Day:
  Washed cells with DPBS
  Resuspended cells in 4 ml DPBS with 5 mM glucose
  Added 45 µl/well in a 96 well black/white isoplate
  Added 10 µl of 50 µM coelenterazine H in DPBS
  Incubated for 5 minutes
  Added 45 µl of the compound of interest in a 2.5 fold higher dose than desired.
  Incubated at room temperature for 20 minutes
  Read the plate using a luminescence plate reader Results The arrestin recruitment assay was performed on different receptors including β2-adrenergic receptor (B2R)+/−GRK2, Dopamine 2 receptor (D2R)+GRK2 and Mµ opioid receptor (MOR) with increasing concentrations of the agonists isoproterenol, dopamine and DAMGO, respectively. The compound was added in a logarithmic concentration scale and plotted with luminescence counts on the Y-axis and log of the compound concentration on the x-axis (FIG. 4).

Figure 4:
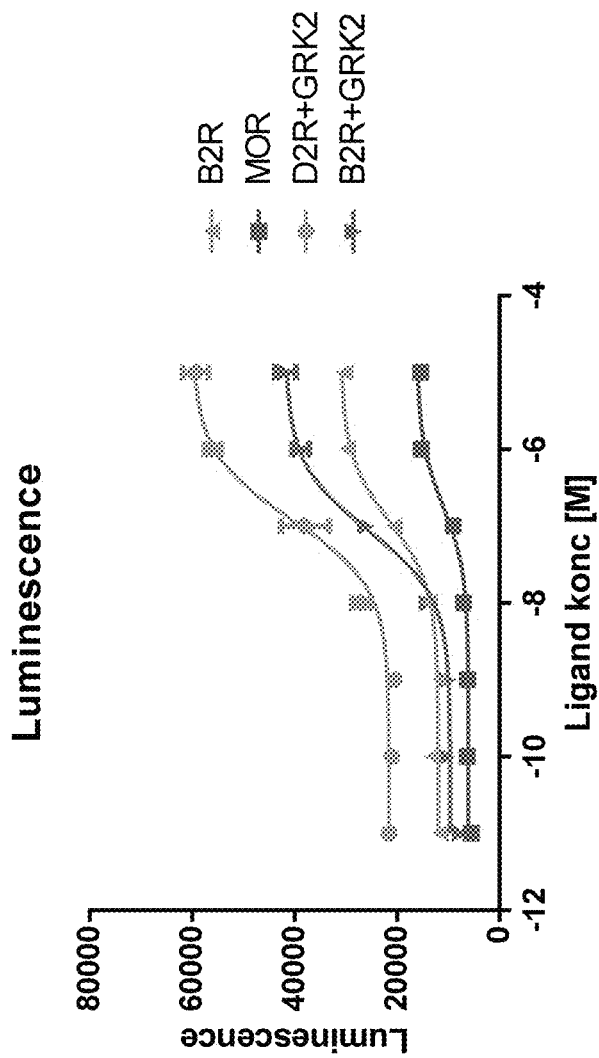
FIG. 4 is a graph showing the results of the using the constructs shown in FIG. 2 to identify a ligand of GPCRs, including β2-adrenergic receptor (B2R)+/−GRK2, Dopamine 2 receptor (D2R)+GRK2 and Mµ opioid receptor (MOR). The Y-axis shows luminescence counts and X-axis shows the log of the compound concentration.

As shown in FIG. 4, the assay to identify ligands using the constructs worked for these receptors with luminescence increasing as the concentration of agonist or ligand of the receptor was increased.

Example 4-β-Arrestin Recruitment Assay in Multiscreen™ Stable Cell Lines

Materials and Methods

Multiscreen™ stable GPCR CHO-K1 cell lines were stably transfected with constructs described in Example 2. CHO-K1 cells used expressed the following GPCRs:
µ opioid receptor (Catalog CA1350-1a);
κ opioid receptor (Catalog CA1352-1a);
δ opioid receptor (Catalog CA1351-1);
Nociceptin opioid receptor (Catalog CA1354a);
b2 Adrenoceptor Catalog (CA1438-1a);
V1A receptor Catalog (CA1042-1);
CB1 receptor pool Catalog (CA1229-1a); and
CB2 receptor Catalog (CA1230-1a).

The final clones were selected by limited dilution and screened directly with arrestin recruitment assay. In the arrestin assay, cells were seeded in white opaque PDL-coated 384-well plates and incubated overnight at 37° C. and 5% $CO_2$. Media was removed and cells were washed with PBS. Coelenterazine H was incubated for 5 minutes at room temperature. Cells were subsequently treated with various dosages of the appropriate ligand for 10 or 20 minutes at room temperature before reading luminescence emissions on a FlexStation III (Molecular Devices).

Results

Figure 5:
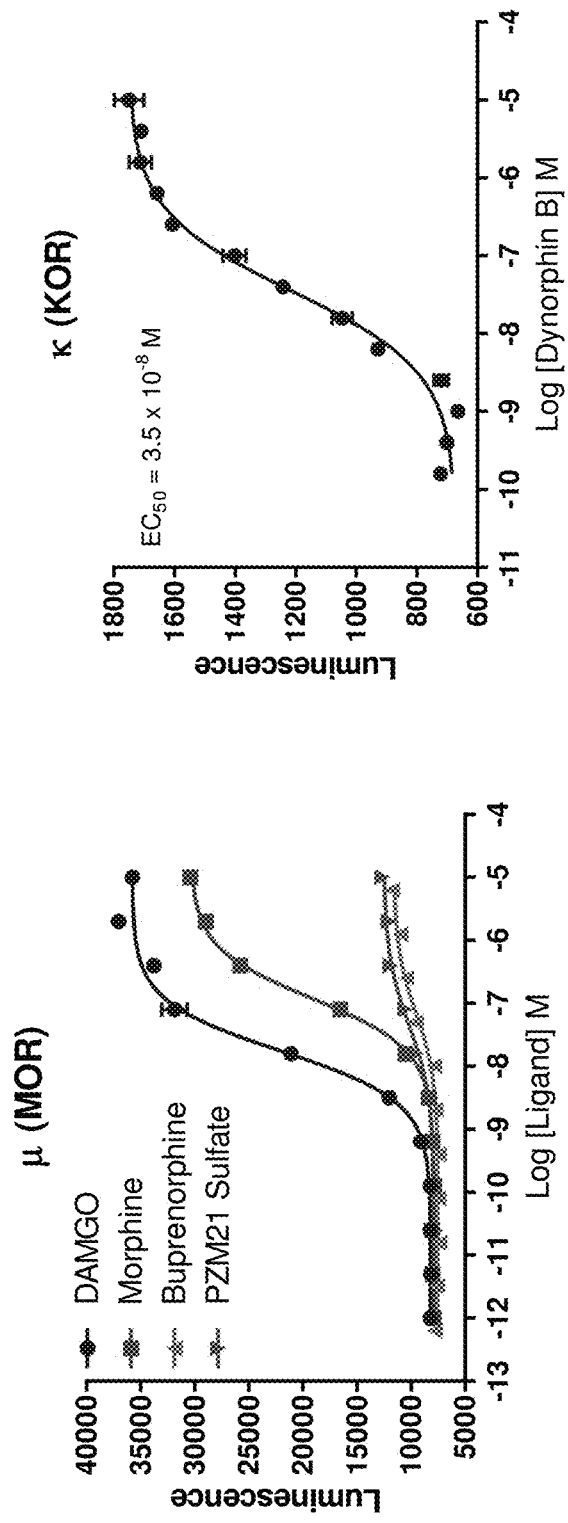
FIG. 5 are graphs showing the results of using the constructs shown in FIG. 2 to identify ligands of additional receptors. The Y-axis shows luminescence counts and X-axis shows the log of the compound concentration
Figure 5:
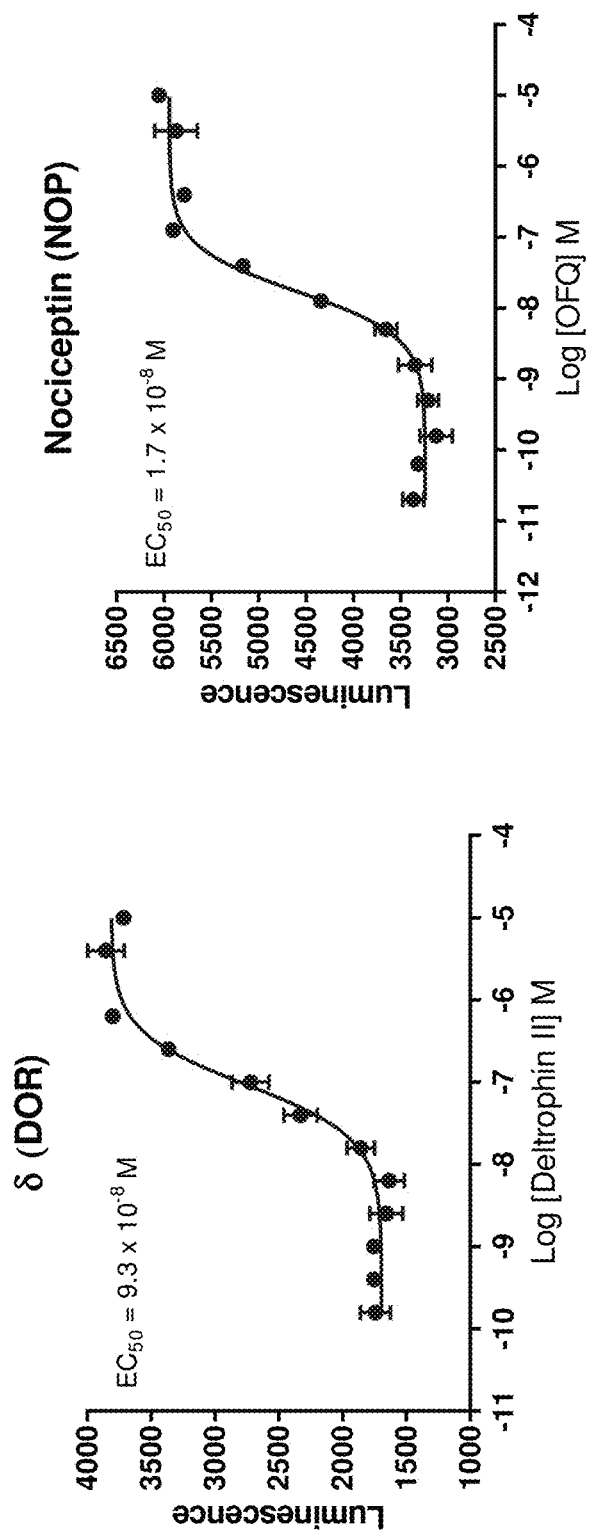
Figure 5:
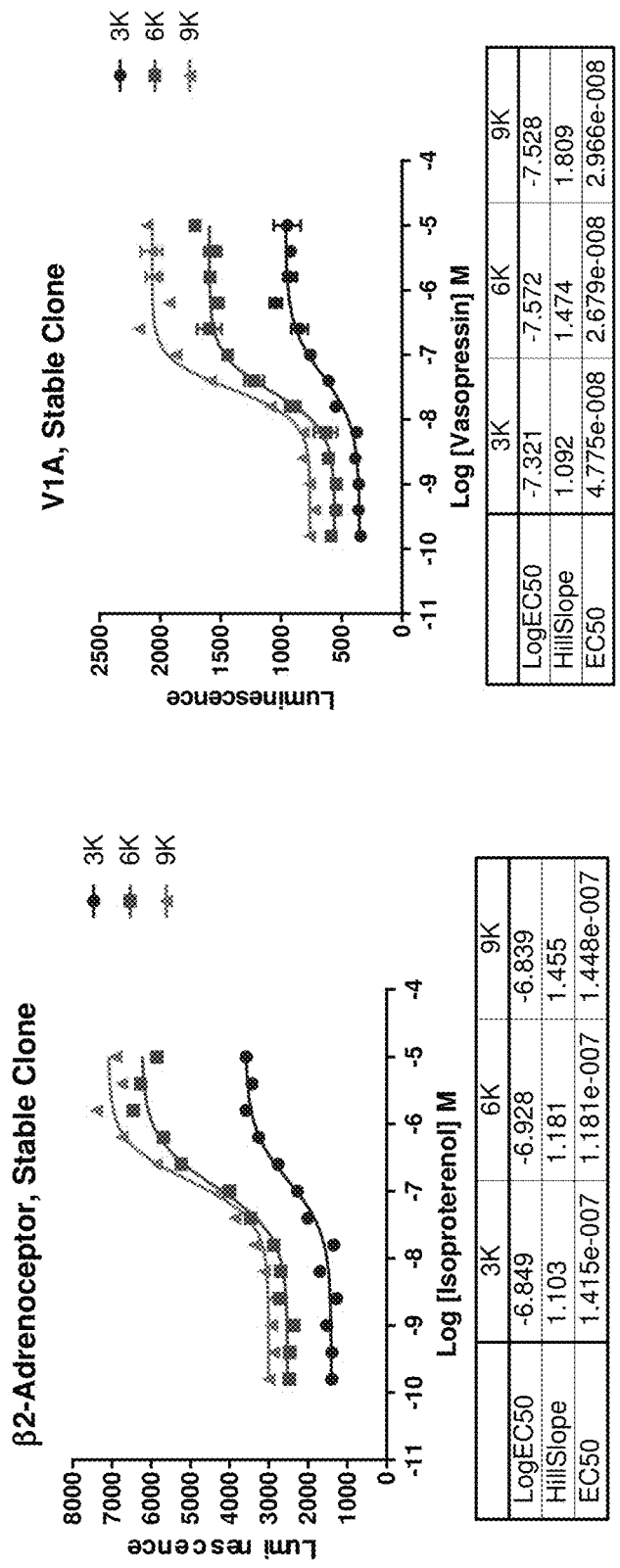
Figure 5:
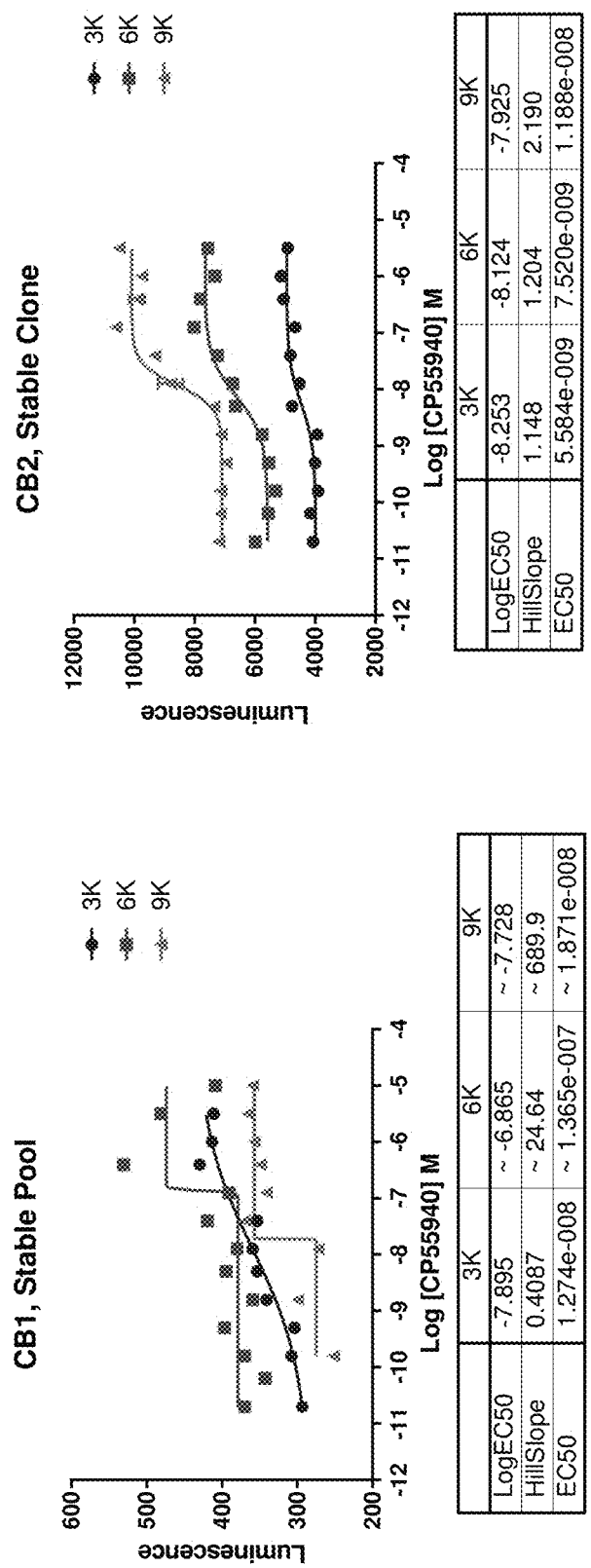

Arrestin results are shown as luminescence values in FIG. 5. Data in graphs are represented in Mean±SD. Dose-dependent responses were fitted with sigmoidal dose-response curves allowing variable slopes using GraphPad Prism version 6 (Graphpad Prism). As expected, luminescence increased as dosage of the ligand increased. Also as shown in the results for MOR, there is no luminescence when controls (non-ligands of the receptor) were used.

---

The invention claimed is:

1. A method for identifying an agonist or an antagonist of a G protein-coupled receptor, comprising:
   a. providing a first polypeptide comprising the amino acid sequence of SEQ ID NO: 2, said first polypeptide is conjugated to a first protein, wherein the first protein is selected from the group consisting of arrestin and G-protein coupled receptor kinase (GRK);
   b. providing a second polypeptide comprising the amino acid sequence of SEQ ID NO: 1, said second polypeptide is conjugated to a second protein, wherein the second protein is in proximity to the receptor and is selected from the group consisting of GAP43, KRas, HRas and CD8, wherein the second polypeptide is capable of interacting with the first polypeptide to form a modified *Oplophorus* luciferase to produce a luminescent signal when a test compound binds the receptor and the first protein moves to the receptor in proximity of the second protein;
   c. contacting a test agent with the receptor;
   d. adding a substrate for *Oplophorus* luciferase; and
   e. detecting a luminescent signal, thereby identifying an agonist or an antagonist of the receptor.

2. The method of claim 1, wherein the first protein is arrestin chosen from the group consisting of arrestin-1, arrestin-2, arrestin-3, and arrestin-4.

3. The method of claim 1, wherein the first polypeptide is conjugated to a first protein by use of a peptide linker.

4. The method assay of claim 1, wherein the second polypeptide is conjugated to a second protein by use of a peptide linker.

5. The method of claim 1, wherein:
   a. the conjugate of the first polypeptide and the first protein comprises the amino acid sequence of SEQ ID NO: 5; and
   b. the conjugate of the second polypeptide and the second protein comprises the amino acid sequence of SEQ ID NO:7.

6. The method of claim 1, wherein the first polypeptide and the first protein are conjugated with a first peptide linker, and wherein the second polypeptide and the second protein are conjugated with a second peptide linker.

7. The method of claim 6, wherein the second peptide linker comprises the amino acid sequence of the linker in SEQ ID NO: 7 or a variant thereof.

* * * * *

UNITED STATES PATENT AND TRADEMARK OFFICE
CERTIFICATE OF CORRECTION

| | |
|---|---|
| PATENT NO. | : 10,962,538 B2 |
| APPLICATION NO. | : 16/008834 |
| DATED | : March 30, 2021 |
| INVENTOR(S) | : Javitch et al. |

It is certified that error appears in the above-identified patent and that said Letters Patent is hereby corrected as shown below:

In the Specification

Column 1, Lines 4-6, should read:
-- This invention was made with government support under MH054137 awarded by the National Institutes of Health. The government has certain rights in the invention. --

Signed and Sealed this
Twelfth Day of March, 2024

Katherine Kelly Vidal
*Director of the United States Patent and Trademark Office*